US00PP35029P2

(12) United States Plant Patent
Cain

(10) Patent No.: US PP35,029 P2
(45) Date of Patent: Mar. 14, 2023

(54) GRAPEVINE PLANT NAMED 'IFG RAIS-ONE'

(50) Latin Name: *Vitis vinifera*
Varietal Denomination: IFG Rais-one

(71) Applicant: International Fruit Genetics, LLC, Bakersfield, CA (US)

(72) Inventor: David Cain, Lutz, FL (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 17/876,004

(22) Filed: Jul. 28, 2022

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207, 205
CPC ..... A01H 5/08; A01H 5/00; A01H 6/88
See application file for complete search history.

(56) References Cited

U.S. PATENT DOCUMENTS

PP26,527 P2 * 3/2016 Ramming ..... A01H 6/88
Plt./205

* cited by examiner

*Primary Examiner* — June Hwu

(57) ABSTRACT

This invention is a new and distinct grapevine plant denominated 'IFG Rais-one'. The new grapevine is characterized by producing small-sized white seedless berries that begin to dehydrate naturally on the vine, producing dried on the vine raisins without the need for cane-cutting. Berries are borne on medium sized clusters which are loose in nature.

2 Drawing Sheets

Latin name of the genus and species claimed: *Vitis vinifera.*

Variety denomination: 'IFG Rais-one'.

BACKGROUND OF THE INVENTION

The new and distinct Grapevine plant described and claimed herein originated from a hand pollinated cross of IFG 03002-074-146 (unreleased) and IFG 04081-029-066 hybridized in May 2011. The present variety of grapevine was selected as a single plant in August 2013 and was first asexually propagated by hardwood cuttings in December 2013 near Delano, Kern County, Calif. These resulting cuttings produced second generation plants that were planted during April 2014 near Delano, Kern County, Calif. and were observed for four years and found to reproduce true-to-type.

BRIEF SUMMARY OF THE INVENTION

The new grapevine 'IFG Rais-one' is characterized by producing small white berries that are seedless and have thin skin. The variety produces berries that dehydrate naturally on the vine producing dry on the vine raisins that do not require cane-cutting to achieve full raisining. The drying of 'IFG Rais-one' berries typically occurs in August, which is earlier than the predominant raisin variety "Thompson Seedless" in the San Joaquin Valley of California. To the inventor's knowledge, the known variety to which the new grapevine variety is most similar is 'Sunpreme' (U.S. Plant Pat. No. 26,527). IFG Rais-one differs from 'Sunpreme' in not having a muscat flavor and by having a rachis that stays attached to the current year's shoots even when berries are fully dehydrated.

'IFG Rais-one' differs from its maternal parent, IFG 03002-074-146, by producing white berries as opposed to red berries, as well as having a smaller seed trace. It differs from its pollen parent IFG 04081-029-066, by being earlier ripening, naturally dry on the vine without the need for cane cutting, and not possessing a muscat aroma.

BRIEF DESCRIPTION OF THE DRAWING

The accompanying photographic drawings illustrate in full color 'IFG Rais-one'. The photographic drawings were taken outdoors with indirect lighting. The colors are as nearly true as is reasonably possible in a color representation of this type.

DETAILED BOTANICAL DESCRIPTION OF THE INVENTION

Figure 1:
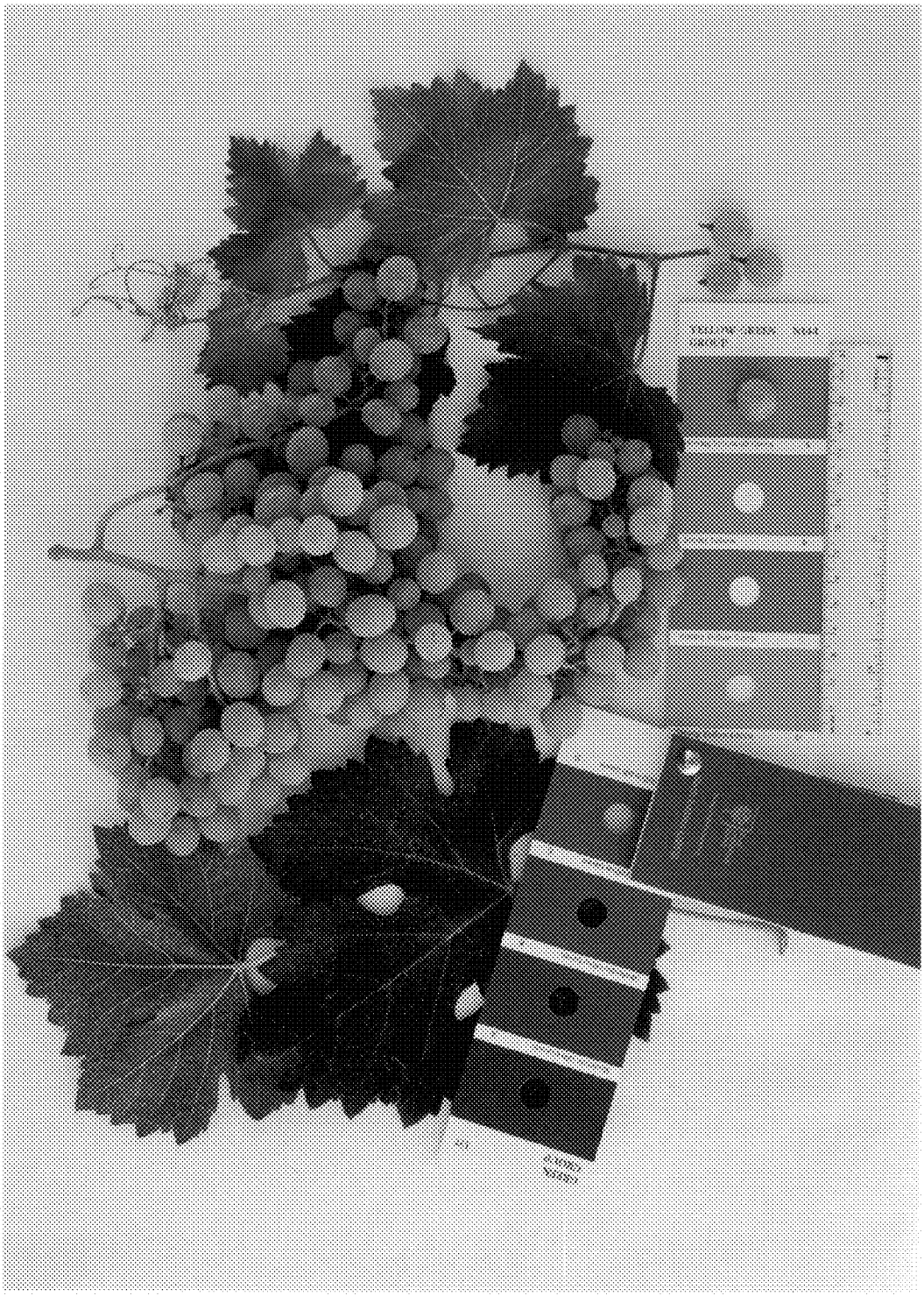
FIG. 1—The left side of the drawing has a mature leaf. A mature fruit cluster is represented in the center of the drawing. A young shoot tip can be seen on the right side of the drawing along with a typical berry in cross section.
Figure 2:
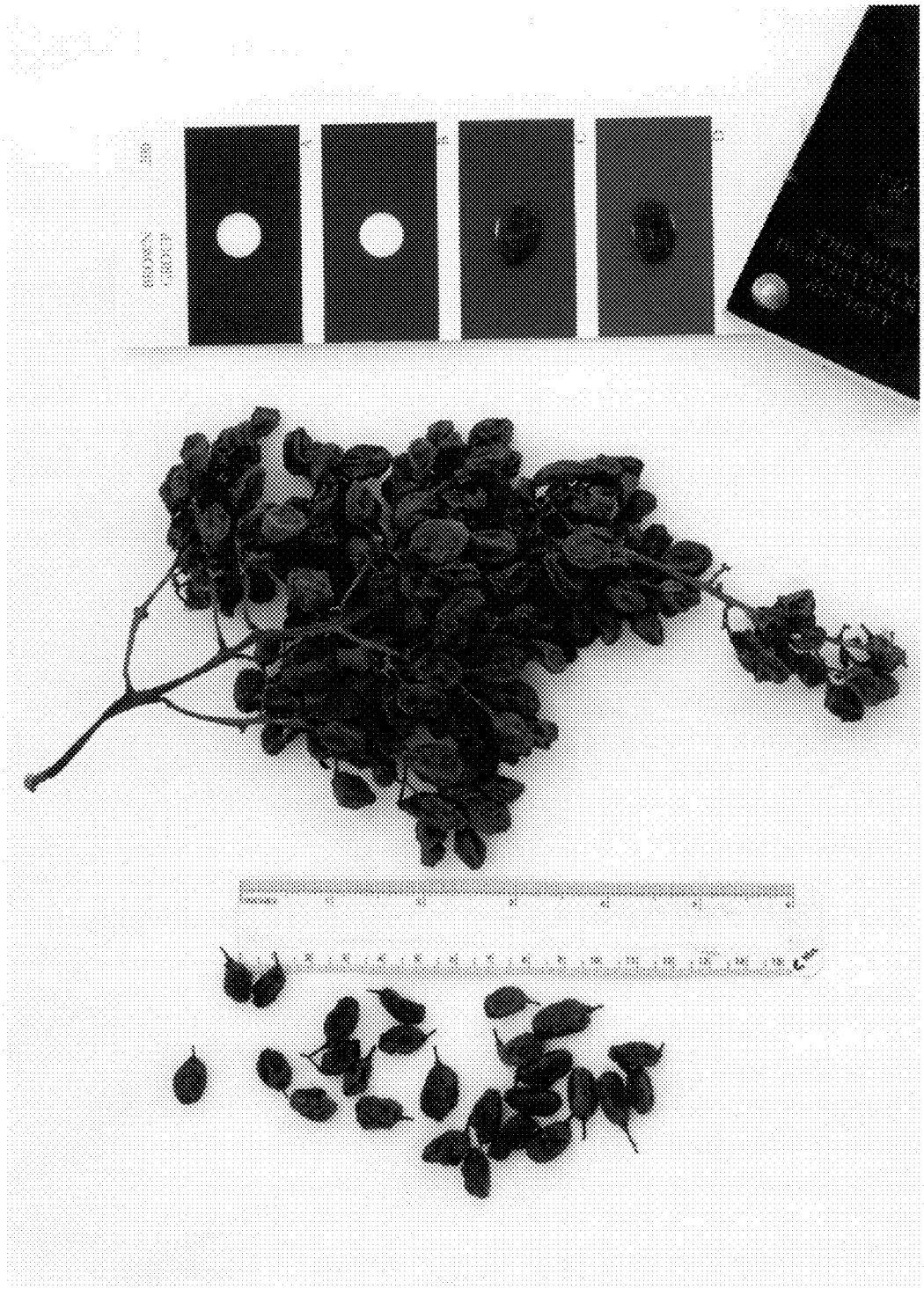
FIG. 2—Shows in full color 'IFG Rais-one' as a dry product. Individual dried berries can be seen on the left side of the drawing along with an entire dried fruit cluster in the center of the drawing.

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Rais-one' plants grown in the vicinity of Delano, Kern County, Calif. during 2018 and 2019, and is believed to apply to plants of the variety grown under similar conditions of soil and climate elsewhere:

VINE

General:

*Vigor.*—Moderate to vigorous.
*Density of foliage.*—Dense.
*Productivity.*—Productive: producing approximately 4.7 to 7.4 kg of dried fruit per vine.
*Root stock.*—Own root.
*Training method.*—Typically spur pruned leaving 2 bud spurs.
*Resistance/susceptibility to typical pests and disease of Vitis vinifera species.*—not observed to date.
*Hardiness zone.*—Fully hardy in USDA zone 9A (2012). Not tested in other zones.

Trunk:

*Trunk diameter of* 4-*year-old vines at* 30 *cm above the soil line.*—About 4.8 cm.
*Shape.*—Medium.
*Surface texture.*—Medium rough texture.
*Inner bark color.*—Greyed-orange: 165A.
*Outer bark color.*—Brown: N200C.

SHOOTS

Young shoot:

*Form of tip.*—Wide open.
*Distribution of anthocyanin coloration of tip.*—Absent.
*Intensity of anthocyanin coloration of tip.*—Absent.
*Density of prostrate hairs of tip.*—Dense.
*Density of erect hairs on tip.*—Absent.
*Color.*—Yellow-green: 145A.

Woody shoot (mature canes):

*Internode length.*—Long: About 10.3 cm.
*Width at node.*—About 1.1 cm.
*Cross section.*—Circular to somewhat elliptic.
*Surface.*—Striate.
*Main color.*—The following colors were observed: Greyed-orange: 166B and 166C and 166D.
*Density of erect hairs on nodes.*—Sparse.
*Density of erect hairs on internodes.*—Sparse.
*Axillary shoot length at full bloom.*—Weak: Approximately 8.5 cm.

Flowering shoot:

*Vigor during flowering.*—Medium to strong.
*Attitude during flowering on shoots not tied.*—Semi-erect.
*Color-dorsal side of internodes.*—Yellow-green: 144A.
*Color-ventral side of internodes.*—Yellow-green: 144A.
*Color-dorsal side of nodes.*—Yellow-green: 144A.
*Color-ventral side of nodes.*—Yellow-green: 144A.
*Density of prostrate hairs on nodes.*—Sparse.
*Density of erect hairs on nodes.*—None.
*Density of prostrate hairs on internode.*—Sparse.
*Density of erect hairs on internode.*—None.
*Anthocyanin coloration of buds.*—Absent.

Tendrils:

*Distribution on the shoot* (*at full flowering*).—Discontinuous.
*Length of Tendril.*—Medium: About 16.7 cm.
*Thickness of tendril* 2 *cm from base.*—About 1.4 mm.
*Color.*—Yellow-green: 145A and 151A.
*Form.*—Trifurcated and quadfurcated.
*Number of consecutive tendrils.*—2.

LEAVES

Young leaves:

*Color of upper surface of first four distal unfolded leaves.*—Yellow-green: 145A.
*Color of lower surface of young leaves.*—Yellow-green: 145B.
*Average intensity of anthocyanin coloration of six distal leaves prior to flowering.*—Absent.
*Density of prostrate hairs between veins* (*lower surface*).—Moderately dense.
*Density of prostrate hairs on veins* (*lower surface*).—Moderately dense.
*Density of erect hairs between veins* (*lower surface*).—Absent.
*Density of erect hairs on veins* (*lower surface*).—Absent.

Mature leaves (opposite first cluster):

*Average length.*—About 13.9 cm.
*Average width.*—About 14.1 cm.
*Mature leaf size.*—Medium.
*Shape of blade.*—Wedge-shaped.
*Number of lobes.*—5.
*Blade venation.*—Palmate.
*Anthocyanin coloration of main veins on upper side of blade.*—Absent.
*Mature leaf profile.*—Undulate.
*Blistering surface of blade upper surface.*—Very weak.
*Leaf blade tip.*—In the plane of the leaf.
*Leaf apex.*—Broadly acute.
*Leaf margin.*—Serrate.
*Undulation of margin.*—Medium.
*Undulation of blade between main and lateral veins.*—Slight.
*Shape of teeth.*—Mixture of both sides straight and both sides convex.
*Length of teeth.*—Medium: About 0.4 cm.
*Width of teeth.*—About 1.1 cm.
*Ratio length/width of teeth.*—Medium.
*Shape of upper lateral sinuses.*—Closed to lobes slightly overlapping.
*Depth of upper lateral sinuses.*—Medium to deep: Approximately 4.6 cm.
*General shape petiole sinus.*—Half open.
*Shape of base of upper leaf sinuses.*—U-shaped.
*Tooth at petiole sinus.*—Absent.
*Density of prostrate hairs between veins on lower surface of blade.*—Medium.
*Density of erect hairs between veins on lower surface of blade.*—Absent.
*Density of prostrate hairs on main veins on lower surface of blade.*—Medium.
*Density of erect hairs on main veins on lower surface of blade.*—Very sparse.
*Density of prostrate hairs on main veins on upper surface of blade.*—Sparse.

*Density of erect hairs on main veins on upper surface of blade.*—None.
*Autumn coloration of leaves.*—Yellow: 11A.

Upper surface:
*Color.*—Green: 137A.
*Anthocyanin coloration of main veins (lower surface).*—Absent.
*Color of main veins.*—Yellow-green: 145A.
*Surface appearance.*—Dull.
*Blistering surface of blade.*—Very weak.

Lower surface:
*Color.*—Green: 137C.
*Anthocyanin coloration of main veins (lower surface).*—Absent.
*Color of main veins.*—Yellow-green: 145C.
*Glossiness.*—Weak.
*Surface texture.*—Smooth.
*Surface appearance.*—Dull.

Petiole:
*Length.*—About 13.1 cm.
*Diameter of petiole 2 cm from blade.*—About 2.6 mm.
*Petiole color.*—Yellow-green: 145C.
*Length of petiole compared to middle vein.*—Slightly shorter.
*Density of prostrate hairs on petiole.*—Sparse.
*Density of erect hairs on petiole.*—None.

Buds:
*Bud fruitfulness.*—Basal: mostly fruitful.
*Position of first fruitful shoot on previous season cane.*—$1^{st}$ to $2^{nd}$ node.
*Dormant bud length.*—About 4.7 mm.
*Dormant bud width in the proximal/distal plane.*—About 4.1 mm.
*Dormant bud color.*—Greyed-orange: 166A and 166B.
*Time of bud burst.*—About Mar. 15, 2019.

FLOWERS

General:
*Flower sex.*—Hermaphrodite.
*Length of single flower, unopened.*—About 2.7 mm.
*Width of single flower.*—Unopened: About 1.8 mm. Opened: About 3.4 mm.
*Stamen length.*—About 2.7 mm.
*Stamen count.*—5.
*Pollen color.*—Yellow: 10C.
*Pistil length.*—About 2.0 mm.
*Pistil color.*—Yellow-green: 145A.
*Length of first inflorescence.*—Long: About 19.8 cm long by about 9.1 cm wide.
*Position of first flowering and fruiting node.*—$2^{nd}$ to $4^{th}$ node (current season growth).
*Number of inflorescence per flowering shoot.*—2.1 to 3: About 2.4.
*Time of bloom.*—Medium as compared with similar varieties in the growing area of Delano, Calif.
*Date of full bloom.*—About May 10, 2019.

FRUIT

General:
*Ripening period.*—Ripe, average to soft berries just prior to the onset of fruit wilting: About Jul. 17, 2018.
*Use.*—Raisin, no fresh table grape evaluations were performed to evaluate the suitability of this variety as a table grape.
*Refractometer test.*—Soluble solids: about 23.4 Brix.
*Brix/acid.*—About 41.8.
*Titratable acidity.*—About 0.56.
*Juice pH.*—About 3.40.
*Juice color.*—Yellow-green: 145C.

Cluster:
*Mature cluster length (peduncle excluded).*—About 28.4 cm.
*Mature cluster width.*—About 13.3 cm.
*Mature cluster weight.*—About 419 g.
*Bunch density.*—Medium: densely distributed berries, pedicels not visible, berries movable.
*Number of berries.*—About 254.
*Form.*—Conical.

Peduncle:
*Lignification of peduncle.*—Weak.
*Diameter of peduncle.*—3.9 mm.
*Length of peduncle.*—Short: Approximately 3.2 cm.
*Color of peduncle.*—Yellow-green: 145A.

Berry:
*Uniformity of size.*—Uniform.
*Single berry weight.*—About 2.3 g natural.
*Shape.*—Broad ellipsoid.
*Seeds.*—Seed traces occasionally noticeable.
*Cross section.*—Circular.
*Berry dimensions.*—Longitudinal axis: About 1.6 cm: Horizontal axis: About 1.4 cm.
*Pedicel length.*—About 5.8 mm.
*Pedicel width.*—About 0.9 mm.
*Pedicel color.*—Yellow-green: 145A.
*Berry firmness.*—Average to soft.
*Particular flavor.*—Neutral.
*Bloom (cuticular wax).*—Medium.
*Berry separation from pedicel.*—Medium.
*Skin color (without bloom).*—Yellow-green: N144A.
*Flesh color.*—Green-white: 157A.

Skin:
*Thickness.*—Medium.
*Skin toughness.*—Not notable when chewing.
*Reticulation.*—Absent.
*Tenacity.*—Tenacious to flesh.

Dry product:
*Dried berries (raisins): Average moisture content.*—Less than 9%.
*Raisin length.*—About: 13.6 mm.
*Raisin width.*—About: 8.0 mm.
*Raisin weight.*—Approximately 0.5 gm.
*Raisin color.*—The following colors were observed: Brown: 200C and 200D.
*Raisin flavor.*—Neutral.
*Dry cluster length.*—About 20.1 cm.
*Dry cluster width.*—About 11.0 cm.
*Dry cluster weight.*—About 78.0 gm.
*Raisin yield.*—Approximately 2830 to 4480 kg/acre, assuming a vine density of 605 vines per acre.
*Keeping quality.*—Excellent. Storage characteristics similar to other raisins.
*Raisin quality.*—Approximately 86.1% B or better grade.

What is claimed is:

1. A new and distinct variety of grapevine plant named 'IFG Rais-one', as illustrated and described herein.

* * * * *